(12) United States Patent
Hosono et al.

(10) Patent No.: US 7,235,225 B2
(45) Date of Patent: Jun. 26, 2007

(54) 12CAO·7Al$_2$O$_3$ COMPOUND AND METHOD FOR PREPARATION THEREOF

(75) Inventors: Hideo Hosono, Yamato (JP); Masahiro Hirano, Tokyo (JP); Katsuro Hayashi, Kawasaki (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 272 days.

(21) Appl. No.: 10/492,938

(22) PCT Filed: Oct. 17, 2002

(86) PCT No.: PCT/JP02/10806

§ 371 (c)(1),
(2), (4) Date: Oct. 29, 2004

(87) PCT Pub. No.: WO03/033406

PCT Pub. Date: Apr. 24, 2003

(65) Prior Publication Data

US 2005/0053546 A1    Mar. 10, 2005

(30) Foreign Application Priority Data

Oct. 18, 2001  (JP)  ............................. 2001-321251

(51) Int. Cl.
*C01F 7/00* (2006.01)
*A01N 59/06* (2006.01)
*B01J 23/02* (2006.01)
*H01M 8/10* (2006.01)

(52) U.S. Cl. .................. 423/600; 424/688; 429/30; 429/231.6; 502/341

(58) Field of Classification Search ................ 423/600, 423/115, 579, 594.16; 424/688; 252/184; 73/19.01; 502/341; 204/424; 429/27, 29, 429/33, 231.6
See application file for complete search history.

(56) References Cited

FOREIGN PATENT DOCUMENTS

WO    WO01/791115    10/2001

OTHER PUBLICATIONS

R. Stöber; Journal of Solid State Chemistry, vol. 81, pp. 152-164. 1989. Cited in the PCT search rpt.
H. Hosono et al.; Inorganic Chemistry, vol. 26, No. 8, pp. 1192-1195. 1987. Cited in the PCT search rpt.
H. Hosono et al.; Journal of the Material Science Society of Japan, vol. 33, No. 4, pp. 171-172. 1996. Cited in the PCT search rpt.
J. A. Imlach et al.; Cement and Concrete Research, vol. 1, pp. 57-61. 1971. Cited in the PCT search rpt.
Patent Abstracts of Japan, Pub. No. 2002-316867, dated Oct. 31, 2002.
H. Sango et al.; Journal of the Ceramic Society of Japan, vol. 102, No. 8, pp. 772-777. 1994.
Von Hnas Bartl et al; N. Jahrbuch F. Mineralogie. Monastshefre 1970. pp. 547-552.

*Primary Examiner*—Wayne A. Langel
*Assistant Examiner*—James Fiorito
(74) *Attorney, Agent, or Firm*—Westerman, Hattori, Daniels & Adrian, LLP.

(57) ABSTRACT

There is provided a C12A7 compound capable of selectively and reversibly clathrating X$^-$ ions, such as active oxygen radicals, with improved controllability. The C12A7 compound clathrating OH$^-$ ions and On$^-$ at a concentration of $2 \times 10^{19}$ cm$^{-3}$ or less can be prepared by subjecting a mixed material containing Ca and Al to a solid phase reaction at a firing temperature not lower than 1200° C. and lower than 1449° C. in a dry oxygen atmosphere having an oxygen partial pressure of 0.1 atm or more and a water vapor partial pressure of 10$^{-3}$ atm or less, keeping the resultant product at a temperature of 1200° C. or higher, and cooling rapidly. The C12A7 compound is heat-treated to clathrate OH$^-$ ions at a concentration of $2 \times 10^{19}$ cm$^{-3}$ or less, and On$^-$ at a high concentration of more than $2 \times 10^{19}$ cm$^{-3}$. The compound can reversibly clathrate or release On$^-$ ion radicals through the elevation or lowering of the temperature thereof in a temperature range of 300 to 850° C. The compound is useful for an oxidation catalyst, an anti-bacterial agent, an ion conducting material, an electrode for a solid-electrolyte fuel cell, and the like.

5 Claims, 5 Drawing Sheets

12CAO·7Al₂O₃ COMPOUND AND METHOD FOR PREPARATION THEREOF

TECHNICAL FIELD

The present invention relates to a 12CaO.7Al₂O₃ compound (referred to as C12A7) including a controlled amount of clathrated oxygen radicals represented by On⁻ and OH⁻ ions, a method for the preparation thereof, and an application thereof. More particularly, the present invention relates to C12A7 including monovalent anions represented by X⁻ and anion molecules at a low concentration, a method for the preparation thereof, a method of selectively and reversibly adding and releasing On⁻ ions to/from the compound with controllability, and an application of the C12A7 compound including a large amount of On⁻. The On⁻ herein refers to O⁻ ion radicals and $O_2^-$ ion radicals, where n is an integer of 1 or 2.

BACKGROUND ART

In 1970, H. B. Bartl et al., stated that in a 12CaO.7Al₂O₃ crystal, two oxygen atoms of 66 oxygen atoms in a unit cell having two molecules do not belong to the network, but exist as "free oxygen" in a cage in the crystal (H. B. Bartl and T. Scheller, Neuses Jarhrb. Mineral., Monatsh. 1970, 547).

Hosono et al., of the present inventors discovered that 12CaO.7Al₂O₃ crystal clathrates $O_2^-$ ion radicals at a concentration of about $1\times10^{19}$ cm⁻³ as measured by electron spin resonance. The 12CaO.7Al₂O₃ crystal was synthesized by subjecting a mixed material containing CaCO₃ and Al₂O₃ or Al(OH)₃ to a solid phase reaction at a temperature of 1200° C. in air. Hosono et al., proposed a model in which part of the free oxygen exists in the cage in the form of $O_2^-$ ion radicals (H. Hosono and Y. Abe, Inorg. Che. 26, 1193, 1987, "Materials Science", Vol. 33, No. 4, pp. 171-172, 1996).

The present inventors subjected a mixed material containing calcium and aluminum at an atomic equivalent ratio of about 12:14 to a solid phase reaction under a controlled atmosphere and temperature, whereby a 12CaO.7Al₂O₃ compound clathrating active oxygen at a high concentration of 10²⁰ cm⁻³ or more was found. The present inventors filed patent applications of the compound itself, a method for production thereof, a measure for taking clathrated ions, a method of identification of active oxygen ion radicals, and an application of the compound (Japanese Patent Application Publication No. 2001-49524=Japanese Unexamined Patent Application Publication No. 2002-003218, PCT/JP01/03252=WO 01/79115 A1).

The present inventors synthesized a C12A7 compound containing OH⁻ ions at a concentration of 10²¹ cm⁻³ or more by hydrating the powder of the 12CaO.7Al₂O₃ compound in water, a water-containing solvent, or a water vapor-containing gas and firing it under an oxygen atmosphere, and filed patent applications of the compound itself, a method for production thereof, a method of identification of OH⁻ ions, and an application of the compound (Japanese Patent Application Publication No. 2001-117546).

As to the mechanism by which the C12A7 compound includes the active oxygen ion radicals at a high concentration, the present inventors consider that the free oxygen in the C12A7 compound is reacted reversibly with the oxygen molecules entering the C12A7 compound. As to the mechanism by which the OH⁻ ions are included at a high concentration, the present inventors consider that the free oxygen in the C12A7 compound is reacted reversibly with the water molecules entering the C12A7 compound. These mechanisms are described below in detail.

Figure 1:
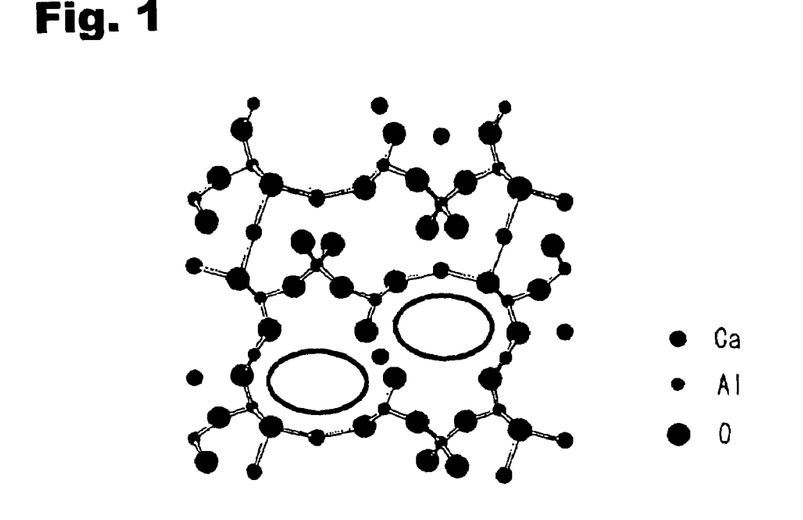
FIG. 1 is a schematic view showing the crystal structure of $12CaO.7Al_2O_3$ (C12A7 compound).

FIG. 1 is a schematic view showing the crystal structure of 12CaO.7Al₂O₃. 12CaO.7Al₂O₃ is a cubic crystal system (lattice constant=11.97 angstrom) belonging to a space group of 143d, including two formula of C12A7 per unit cell, and having a melting point of 1449° C. The crystal has a structure in which Ca²⁺ ions are coordinate with a network structure where tetrahedrons of AlO₄ are aggregated. There is a cavity, i.e., a cage, in the crystal lattice.

$2(12CaO.7Al_2O_3) = Ca_{24}Al_{28}O_{66} = [Ca_{24}Al_{28}O_{64}]^{4+} \cdot 2O^{2-}$ $O_2^-$ ion is called free oxygen, and exists in the cage. In general, $O_2^-$ is always coordinated in the form of a cation in a solid structure, and does not exist in the free state. However, the O²⁻ ions in the cage of the 12CaO.7Al₂O₃ crystal cannot be combined with the cations, and exist in the free state. This state is similar to the case that the ions are adsorbed on a solid surface, and is considered to be very chemically active.

The O²⁻ ions clathrated in the cage are prevented from directly reacting with the external atmosphere. However, when the temperature increases, the case size becomes large due to thermal expansion. Oxygen molecules in the atmosphere can pass through a bottle neck of the cage, to be thus clathrated in the cage. As a result, the reaction proceeds as follows:

O²⁻(in the cage)+O₂(in the cage)=O⁻(in the cage)+ $O_2^-$(in the cage)

Through this reaction, the C12A7 compound clathrates a large amount of active oxygen ion radicals.

Two On⁻ ion radicals are produced from two oxygen ions O²⁻ in the unit cell. The 12CaO.7Al₂O₃ compound clathrating On⁻ ion radicals at a high concentration is described as $[Ca_{24}Al_{28}O_{64}]^{4+} \cdot (2-m)O^{2-}(2m)On^-$. In this formula, $m \leq 2$, and On⁻ ion radicals and O²⁻ ions are clathrated in the cage. The oxygen molecules in the cage and in the atmosphere are equilibrated with the oxygen molecules in the atmosphere in a high temperature region in which the oxygen molecules can pass through the bottle neck of the cage. In general, when the temperature increases, the oxygen atoms in the C12A7 decrease in accordance with the Boyle-Charles law. Accordingly, it is considered that the number of active oxygen ion radicals decrease at a higher temperature.

When the synthesized C12A7 contains H₂O, the reaction of $O_2^-$ (in the cage)+H₂) (in the cage or in the interstices of the crystal lattice)=2OH⁻ (in the cage) proceed, thus clathrating OH⁻ ions in the cage. The 12CaO.7Al₂O₃ compound clathrating OH⁻ ions at a high concentration is described as $[Ca_{24}Al_{28}O_{64}]^{4+} \cdot (2-m)O^{2-}(2m)OH^-$. In this formula, $m \leq 2$, and OH⁻ ions and O²⁻ ions are clathrated in the cage. The H₂O molecules in the cage are equilibrated with the water vapor in the atmosphere in a temperature region in which the H₂O molecules can pass through the bottle neck of the cage.

DISCLOSURE OF INVENTION

In an X⁻ ion clathration mechanism, a stoichiometric composition C12A7 is considered as a starting compound for clathrating On⁻ ion radicals and/or OH⁻ ions at a high concentration. However, the existence of the compound and a method of producing the compound are not known. If a C12A7 compound including no X⁻ ions or including X⁻ ions in a low concentration, i.e., a stoichiometric C12A7 compound containing oxygen ions, or a substantially stoichiometric C12A7 compound can be provided, it is expected that the $X^-$ ions, such as the active oxygen ion radicals, are selectively and reversibly clathrated in the compound with improved controllability.

Since the $OH^-$ ions are clathrated stably as compared with $O_2^-$ ions and/or $O^-$ ion radicals, the $OH^-$ ions cannot be released into the atmosphere when they are fired at an elevated temperature of 1200° C. or more for a prolonged time. The total concentration of the $X^-$ ions is at most two times greater than that of the $O^{2-}$ ions. Accordingly, the concentration of the $OH^-$ ions clathrated in the C12A7 compound should be decreased in order to increase the concentration of other clathrated $X^-$ ions such as $On^-$ ion radicals. In other words, if the concentration of the $OH^-$ ions included in the C12A7 compound can be decreased, the concentration of the clathrated $X^-$ ions other than $OH^-$ ions can be decreased.

The present inventors subjected a mixed material containing calcium and aluminum at an atomic ratio of about 12:14 to a solid phase reaction under controlled atmosphere and temperature to prepare a $12CaO.7Al_2O_3$ compound, kept the compound at a temperature of 850° C. or more under a controlled atmosphere for a prolonged time, and then rapidly cooled the compound at a rate of about 100° C./sec or more, whereby C12A17 including $OH^-$ ions and $On^-$ ion radicals at a concentration of $2\times10^{19}$ $cm^{-3}$ or less was prepared.

The compound is analogous to the stoichiometric C12A7 compound having 66 oxygen atoms (two oxygen ions clathrated in two cages and 64 oxygen atoms in the lattice) in a unit cell having two molecules. The compound is kept at a fixed temperature in the range of 300 to 800° C., preferably 400 to 600° C., or at slowly increasing or decreasing temperature under a controlled atmosphere, whereby the active oxygen ion radicals can be reversibly clathrated and released.

The mixed material containing calcium and aluminum at an atomic ratio of about 12:14, preferably mixed material containing calcium carbonate and γ-aluminum oxide at a molar ratio of 12:7, is subjected to a solid phase reaction as a high temperature not lower than 1200° C., and preferably not lower than 1300° C., under an atmosphere having an oxygen partial pressure of $10^{-2}$ MPa or more and a water vapor partial pressure of $10^{-4}$ MPa or less, and preferably an oxygen partial pressure of $10^{-1}$ MPa or more and a water vapor partial pressure of $10^{-5}$ MPa or less, whereby a $12CaO.7Al_2O_3$ compound is provided.

When the resultant compound is slowly cooled at a rate of about 600° C./hr or less, and preferably about 100° C./hr or less, under the atmosphere described above, the compound clathrates $On^-$ ion radicals at a concentration of more than $10^{19}$ $cm^{-3}$ and the $OH^-$ ions at a concentration of $2\times10^{19}$ $cm^{-3}$ or less.

The compound is kept at 850° C. or more, and preferably 900° C. or more, under the atmosphere described above, and is then rapidly cooled to 300° C. or less, preferably room temperature, for example, at a rate of about 100° C./sec or more, whereby the $On^-$ ions have a concentration of $2\times10^{19}$ $cm^{-3}$ or less.

The C12A7 compounds obtained in this way may clathrate monovalent ions represented by $X^-$ and ion molecules at a concentration of $2\times10^{19}$ $cm^{-3}$ or less. Examples of the monovalent ions represented by $X^-$ and ion molecules include $OH^-$, $On^-$, $F^-$, $Cl^-$, $Br^-$, and $Au^-$ ions. The clathrate amounts of the active oxygen $O_2^-$ (n=2) ion radicals and/or $O^-$ (n=1) ion radicals can be analyzed using an electron spin resonance or Raman scattering spectrum technique.

Figure 2:
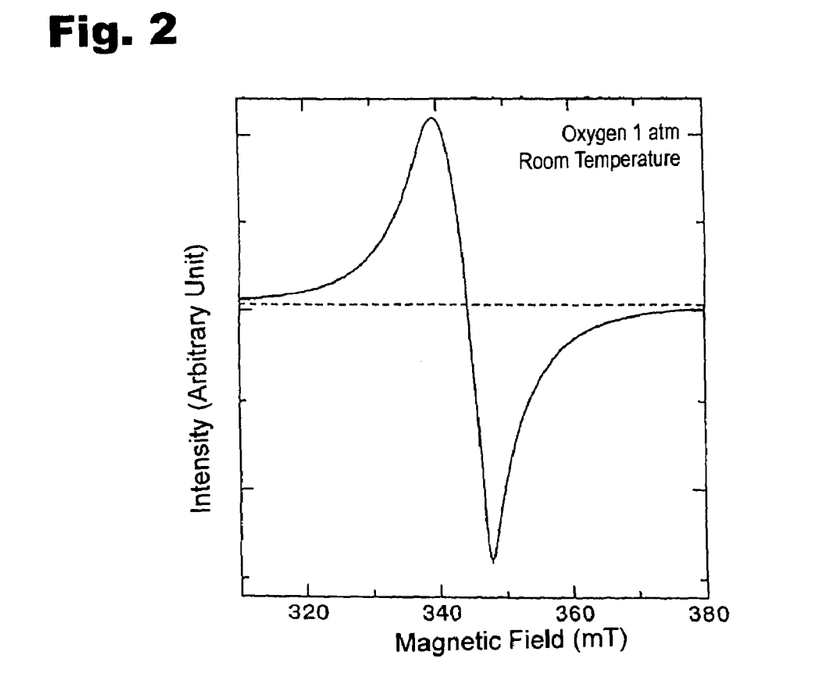
FIG. 2 is a graph showing an example of an electron spin resonance spectrum of the C12A7 compound including On ion radicals at room temperature.
Figure 3:
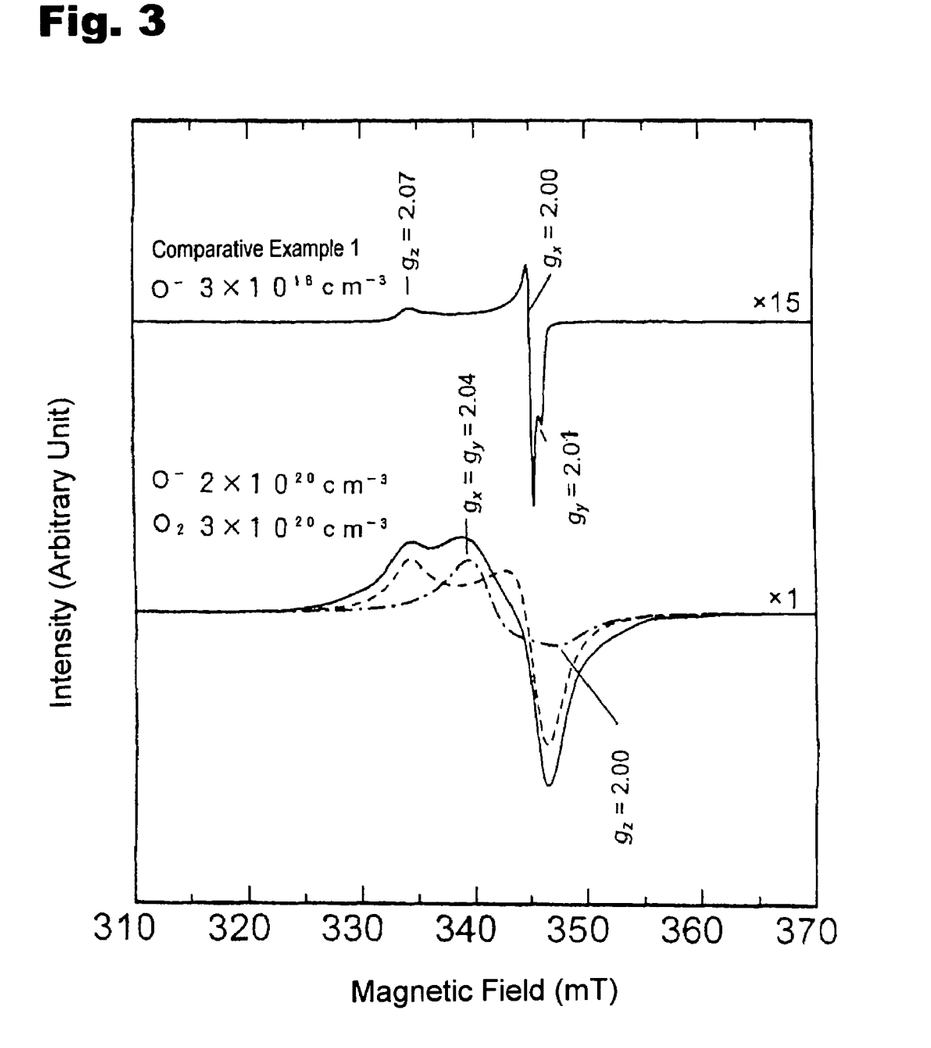
FIG. 3 shows graphs of examples of electron spin resonance spectra of the C12A7 compound including only the 0 ion radicals ($3\times10^{18}$ $cm^{-3}$), and the C12A7 compound including both the $O^-$ ion radicals ($2\times10^{20}$ $cm^{-3}$) and $O_2^-$ ion radicals ($3\times10^{20}$ $cm^{-3}$) at 77K.

FIGS. 2 and 3 show electron spin resonance spectra of the C12A7 compound clathrating $On^-$ ion radicals at room temperature and 77K, respectively. The microwave frequency used was 9.75 GHz. At room temperature, an absorption band g=2.02 having a symmetric shape peaking at a magnetic field of 343 mT is observed. Using the absorption intensity, the concentration of the clathrated $On^-$ ion radicals can be quantified. In the 77K absorption band, some structure is observed. The absorption band is provided by superposing an absorption band of the $O_2^-$ ion radicals defined by gx=2.00, gy=2.01, and gz=2.07 on an absorption band of the $O^-$ ion radicals defined by gx=gy=2.04, and gz=2.00. Based on the intensity of each absorption band, the concentration of clathrated $O_2^-$ ion radicals and $O^-$ ion radicals can be quantified.

Figure 4:
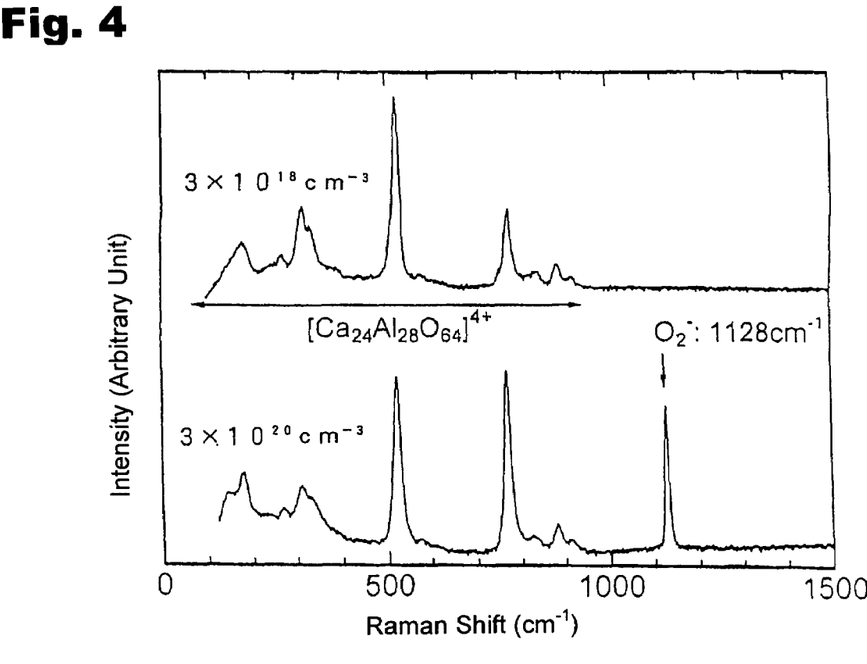
FIG. 4 shows graphs of examples of Raman scattering spectra of the C12A7 compound including $O_2^-$ ion radicals at a concentration of $3\times10^{20}$ $cm^{-3}$.

FIG. 4 shows Raman scattering spectra of the C12A7 compound clathrating the $O_2^-$ ion radicals at a concentration of $3\times10^{18}$ $cm^{-3}$ and $3\times10^{20}$ $cm^{-3}$ at room temperature. The concentration of the $O_2^-$ ion radicals was quantified separately by electron spin resonance absorption band intensity. In the C12A7 compound including the $O_2^-$ ion radicals at a concentration of $3\times10^{20}$ $cm^{-3}$, a Raman shift of 1128 $cm^{-1}$ is due to the peak of the $O_2^-$ ion radicals. Using the Raman peak intensity, the amount of clathrated $O_2^-$ ion radicals can be quantified. The concentration of the clathrated $OH^-$ ions can be analyzed using infrared absorption spectrum and Raman scattering spectrum techniques.

Figure 5:
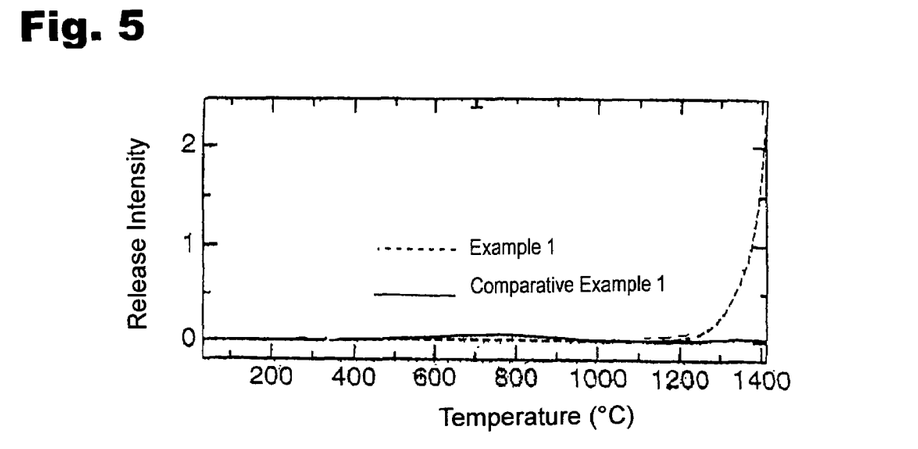
FIG. 5 shows graphs of examples of infrared absorption spectra of $OH^-$ ions near 3560 $cm^1$.
Figure 6:
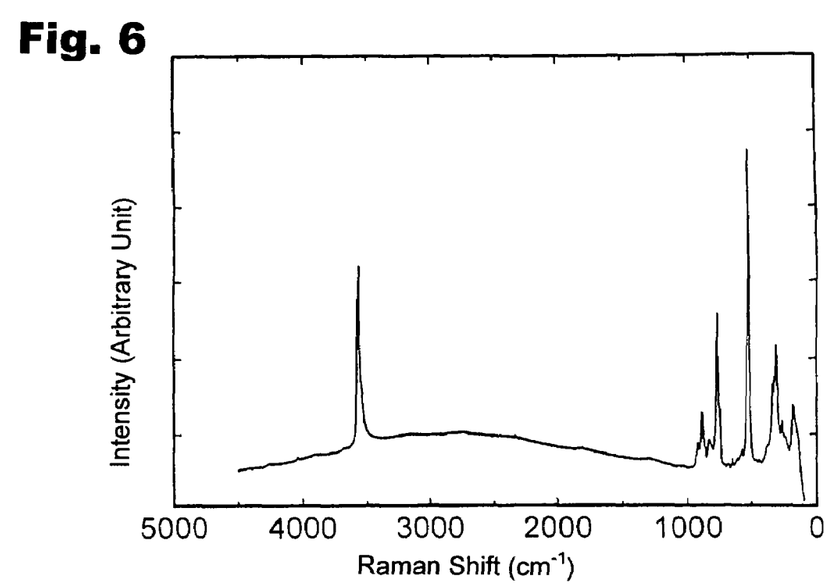
FIG. 6 shows a graph of an example of a Raman scattering peak of $OH^-$ ions near 3500 $cm^{-1}$.

FIG. 5 shows infrared absorption spectra of the C12A7 compound clathrating $OH^-$ at room temperature. Near 3550 $cm^1$, an absorption band due to the $OH^-$ is observed. From this absorption band, the concentration of the $OH^-$ ions can be quantified using a molar extinction coefficient $\epsilon$. The molar extinction coefficient $\epsilon$ is 90 $mol^{-1}$ $dm^3$ $cm^{-1}$. FIG. 6 shows a Raman scattering spectrum of the C12A7 compound clathrating $OH^-$ ions at room temperature. The peak of a Raman shift due to the $OH^-$ ions is near 3500 $cm^1$. Using the peak intensity, the concentration of the $OH^-$ ions can be quantified. The concentration of the $OH^-$ ions can be quantified using a nuclear magnetic resonance spectrum. On the other hand, the C12A7 will clathrate $F^-$, $Cl^-$, $Br^-$, and $Au^-$ ions only when they are intentionally added.

When the water vapor partial pressure upon firing is $10^{-4}$ MPa or more, the concentration of the clathrated $OH^-$ ions exceeds $2\times10^{19}$ $cm^{-3}$. When the compound is fired at 1200° C. or more under an atmosphere with an oxygen partial pressure of $10^{-2}$ MPa or more and a water vapor partial pressure of $10^{-4}$ MPa or less, and preferably an oxygen partial pressure of $10^{-1}$ MPa or more and a water vapor partial pressure of $10^{-5}$ MPa or less, the concentration of the $OH^-$ ions can be decreased. In this case, the compound should be kept at this temperature for a prolonged time.

If the firing temperature is less than 1200° C., the $12CaO.7Al_2O_3$ compound is not well synthesized, even if the compound is fired under an atmosphere having an oxygen partial pressure of $10^{-2}$ MPa or more and a water vapor partial pressure of $10^{-4}$ MPa or less. If the firing temperature exceeds 1449° C., the raw material melts, whereby the $12CaO.7Al_2O_3$ compound is not well synthesized. When the $12CaO.7Al_2O_3$ compound is synthesized by the solid phase reaction, calcium carbonate and γ-aluminum oxide are suitable for the raw material. Also, the compound can be synthesized using a combination of calcium hydroxide or calcium oxide with aluminum hydroxide or various aluminum oxides (α, δ, θ phases).

The electron spin resonance spectrum of the $12CaO.7Al_2O_3$ compound including the active oxygen ion radicals at 77K is provided by superposing a spectrum defined by gx=2.00, gy=2.01, and gz=2.07 on a spectrum defined by gx=gy=2.04, and gz=2.00. Since these g values correspond to the g values of the $O_2^-$ ion radicals and the $O^-$ ion radicals in the solid, it is concluded that the $12CaO.7Al_2O_3$ compound clathrates the $O_2^-$ ion radicals and the $O^-$ ion radicals.

The ESR absorption band is symmetric at room temperature, and is asymmetric at a low temperature of 77K. This corresponds to the fact that the $O_2^-$ ion radicals and the $O^-$ ion radicals rotate in the cage at room temperature but are combined electrostatically with $Ca^{2+}$ ions on the walls of the cage and fixed spatially. Using the absorption intensity, the concentration of the $O_2^-$ ion radicals and the $O^-$ ion radicals can be quantified.

The Raman scattering spectrum of the compound has a strong scattering peak near 1130 $cm^{-1}$. This peak corresponds to the Raman shift of the $O_2^-$ ion radicals, which was reported by K. Nakamoto et al.,(K. Nakamoto, Infrared and Raman Spectra of Inorganic and Coordination Compounds, 1978, Wiley). The ESR absorption band correlates with the Raman scattering intensity. Using Raman scattering intensity, the intensity of the clathrated $O_2^-$ ion radicals can be quantified.

The C12A7 compound including the $On^-$ ion radicals at a high concentration of more than $2\times10^{19}$ $cm^{-3}$ includes $OH^-$ ions at a concentration of only $2\times10^{19}$ $cm^{-3}$ or less. The concentration of the $OH^-$ ions can be quantified using the infrared absorption spectrum near 3560 $cm^{-1}$ (Japanese Patent Application No. 2001-117546).

The resultant C12A7 compound including the $OH^-$ ions at a clathrate concentration of $2\times10^{19}$ $cm^{-3}$ or less and $On^-$ ion radicals at a clathrate concentration of $2\times10^{19}$ $cm^{-3}$ or less is kept at a fixed temperature in the range of 300 to 850° C., and preferably 400 to 600° C., under a dry oxygen atmosphere having an oxygen partial pressure of $10^{-2}$ MPa or more, and preferably $10^{-1}$ MPa or more, and a water vapor partial pressure of $10^{-4}$ MPa or less, whereby the $On^-$ ion radicals can be included in the compound at a high concentration of more than $2\times10^{19}$ $cm^{-1}$.

Instead of maintaining the compound at the fixed temperature, the C12A7 compound fired at a high temperature under a dry oxygen atmosphere may be cooled. In a temperature range of 300 to 850° C., the compound may be slowly cooled. The slow cooling rate depends on the size of the crystal particles grown by firing the C12A7 compound, and may be approximately 600° C./hr or less.

The $On^-$ ion radicals contained in the C12A7 compound are equilibrated with the oxygen molecules in the atmosphere via the clathrated oxygen molecules. At a high temperature of 300° C. or more, some of the $On^-$ ions are exchanged with the oxygen molecules in the atmosphere. Once the C12A7 compound becomes electrically insulating, the compound takes electrons from the $On^-$ ion radicals in order to keep electrical neutrality. The $On^-$ ions are released into the atmosphere as electric neutral oxygen radicals (O.) or oxygen molecules. When an electric field is applied to the compound to externally supply electrons, the $On^-$ ion radicals can be released into the atmosphere as is.

When the compounds or molecules that are easily oxidized are attached to the surfaces of the $On^-$ ions, the $On^-$ ion radicals, especially the $O^-$ ion radicals oxidize the attached compounds or molecules. In this case, the electrons move from the oxidized compounds or the molecules to the C12A7 compound, whereby the electrical neutrality can be kept. Since the $O_2^-$ ion radicals and/or the $O^-$ ion radicals disposed near the surface are easily moved and released, the compound that is easily oxidized, such as a hydrocarbon compound, is oxidized even at a temperature lower than 300° C.

In other words, since the oxidation occurs on the surface of the C12A7 compound at a temperature lower than 300° C., the C12A7 compound can be used as an oxidation catalyst or an antibacterial agent that can act at a temperature lower than 300° C.

The $On^-$ ion radicals clathrated in the C12A7 are taken by the electric field. Alternatively, when the $On^-$ ion radicals are consumed by the reaction with the oxidized material, $O_2$ in the atmosphere is taken into the C12A7 and is reacted with $O_2^-$ ions to produce the $On^-$ ion radicals.

Thus, when the C12A7 compound is kept at 300 to 850° C., the compound functions to convert the oxygen molecules in the atmosphere to $O_2^-$ ion radicals and/or $O^-$ ion radicals. Accordingly, when the compound is kept in the oxygen-containing atmosphere, an oxidation catalytic action can be continued. When exhaust gas containing oxygen emitted from an automobile engine is contacted with the C12A7 compound, incomplete combustion compounds such as hydrocarbons and carbon particles contained in the exhaust gas can be oxidized. Therefore, the C12A7 compound is effective as a catalyst for purifying the exhaust gas of automobile engine.

Since the $On^-$ ion radicals, oxygen ions or oxygen molecules can be released at a high temperature of 300° C. or more, the $12CaO.7Al_2O_3$ of the present invention can be used to oxidize organic materials. The $On^-$ ion radicals, especially $O^-$ ions are known to have antibacterial properties. Therefore, the $12CaO.7Al_2O_3$ clathrating a large quantity of the $On^-$ ion radicals of the present invention can be used as an antibacterial agent. The oxidation reaction on the surface may be performed at a temperature lower than 300° C.

$On^-$ ion radical, kept within the compound at 850° C. or less, exists relatively freely and can move within the crystal. Therefore, the $12CaO.7Al_2O_3$ of the present invention can be used as an ion conductor. The C12A7 compound clathrating the $X^-$ ions at a concentration of $2\times10^{19}$ $cm^{-3}$ or less, i.e., including the clathrated $On^-$ ion radicals at a high concentration can be used as an ion conductor utilizing the movement of the $On^-$ ion radicals. When the ion conductivity and the ability to oxidize various compounds, both properties exhibited by the present compound, are combined, the present compound can be used as an electrode material for an oxide solid-electrolyte fuel cell.

BEST MODE FOR CARRYING OUT THE INVENTION

Embodiments of the present invention will be described below.

REFERENCE EXAMPLE 1

A mixed material containing calcium carbonate and γ-alumina at a molar ratio of 12:7 was fired at 1300° C. for 2 hours under an atmosphere having a water vapor partial pressure of 10$^{-5}$ MPa or less. Then, the mixed material was transferred to a room temperature region under a dry oxygen atmosphere of 10$^{-1}$ MPa, and was contacted with a water-cooled platinum block disposed therein. The cooling rate in the cooling step was about 100° C./sec. The resultant compound was confirmed to be a 12CaO.7Al$_2$O$_3$ compound by X-ray diffraction.

The OH$^-$ ion concentration contained in the resultant compound was quantified by infrared absorption spectroscopy and Raman scattering spectroscopy, and was found to be 2×10$^{19}$ cm$^{-3}$ or less. The On$^-$ ion radical concentration contained in the resultant compound was quantified by an electron spin resonance spectroscopy, and was found to be 1.5×10$^{19}$ cm$^{-3}$. Thus, it was demonstrated that by rapidly cooling the C12A7 compound to room temperature under the dry oxygen atmosphere, C12A17 including OH$^-$ ions and On$^-$ ions at a concentration of 2×10$^{19}$ cm$^{-3}$ or less was obtained.

EXAMPLE 1

A mixed material containing calcium carbonate and γ-alumina at a molar ratio of 12:7 was fired at 1300° C. for 2 hours under a dry oxygen atmosphere of 10$^{-1}$ MPa having a water vapor partial pressure of 10$^{-5}$ MPa or less, and was slowly cooled at a rate of 600° C./hr under the dry oxygen atmosphere of 10$^{-1}$ MPa. The resultant compound was confirmed to be a 12CaO.7Al$_2$O$_3$ compound by X-ray diffraction. The OH$^-$ ion concentration contained in the resultant compound was quantified by infrared absorption spectroscopy and Raman scattering spectroscopy, and was found to be 2×10$^{19}$ cm$^{-3}$ or less. The On$^-$ ion radicals concentration contained in the resultant compound was quantified by electron spin resonance spectra, and O$_2^-$ ion radical and On$^-$ ion radical concentrations were found to be 3×10$^{20}$ cm$^{-3}$ and 2×10$^{20}$ cm$^{-3}$, respectively. Thus, by slowly cooling the C12A7 compound to room temperature under the dry oxygen atmosphere, the C12A17 including OH$^-$ ions at a concentration of 2×10$^{19}$ cm$^{-3}$ or less and On$^-$ ion radicals at a concentration of 5×10$^{20}$ cm$^{-3}$ was obtained.

EXAMPLE 2

A mixed material containing calcium carbonate and γ-alumina at a molar ratio of 12:7 was fired at 1300° C. for 2 hours under water vapor-containing air (an oxygen partial pressure of 2×10$^{-2}$ MPa and a water vapor partial pressure of 10$^{-4}$ MPa) was further fired at 1300° C. for 2 hours under an atmosphere having a dry oxygen pressure of 10$^{-2}$ MPa, and was slowly cooled at a rate of 600° C./hr under the 1-atm dry oxygen atmosphere. The resultant compound was confirmed to be a 12CaO.7Al$_2$O$_3$ compound by X-ray diffraction.

The OH$^-$ ion concentration contained in the resultant 12CaO. 7Al$_2$O$_3$ compound was quantified by infrared absorption spectroscopy and Raman scattering spectroscopy, and was found to be 2×10$^{19}$ cm$^{-3}$ or less. The O$_2^-$ ion radical concentration clathrated in the compound was quantified by ESR and Raman scattering spectroscopy, and was found to be 3×10$^{20}$ cm$^{-3}$. The O$^-$ ion radical clathrate concentration was verified by ESR spectroscopy, and was found to be 2×10$^{20}$ cm$^{-3}$.

The total amount of the On$^-$ ion radicals clathrated in the 12CaO.7Al$_2$O$_3$ compound obtained in EXAMPLES 1 and 2 was 5×10$^{20}$ cm$^{-3}$, that is, 0.8 per unit cell, which was 20% of the theoretically estimated maximum total value 2+2=4.

Figure 7:
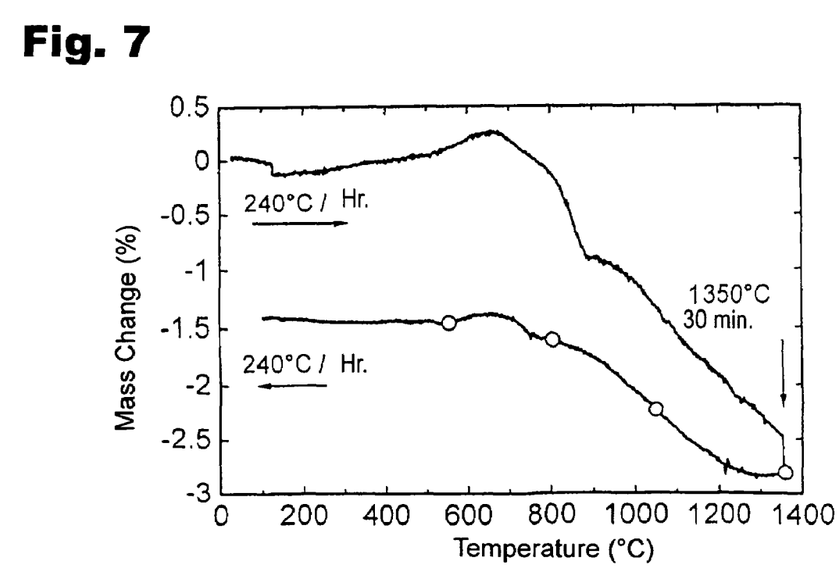
FIG. 7 shows graphs of mass changes by increasing or decreasing the temperature of the 12CaO.7Al$_2$O$_3$ compound in EXAMPLE 1.

The 12CaO.7Al$_2$O$_3$ compound in EXAMPLE 1 was measured for mass changes by increasing or decreasing the temperature under vacuum. FIG. 7 shows the result. The compound obtained in EXAMPLE 1 had reduced mass in a temperature range of 600 to 1350° C. with a temperature increasing curve. Corresponding to the temperature increasing curve, the compound had increased mass in temperature ranges of 1400 to 900° C. and 800 to 600° C. with a temperature decreasing curve.

EXAMPLE 3

Figure 8:
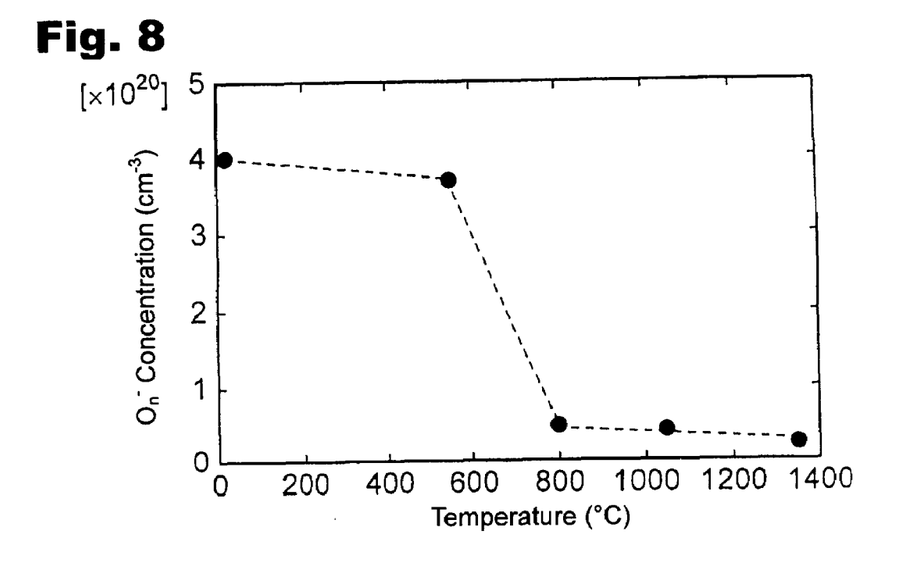
FIG. 8 is a graph showing the On$^-$ ion radicals concentration of the rapid cooled 12CaO.7Al$_2$O$_3$ compound in EXAMPLE 1.

The 12CaO.7Al$_2$O$_3$ compound in EXAMPLE 1 was slowly cooled at a rate of 4° C./min under a dry oxygen atmosphere to each temperature (1350° C., 1050° C., 800° C. and 550° C.) represented by circles in the decreasing temperature curve, was kept at each temperature for 30 minutes, and was then rapidly cooled to room temperature at a rate of about 100° C./sec. The On ion radicals ion concentration contained in each rapidly cooled compound was quantified by electron spin resonance spectroscopy. FIG. 8 shows the resultant On$^-$ ion radicals ion concentration. The concentration represents the amount of the clathrated On$^-$ ion radicals at the temperature when the rapid cooling started.

It was found that clathration of the On$^-$ ions started at about 550° C., the clathration amount thereof was gradually decreased at higher temperature, and the On$^-$ ion radicals were clathrated only at a concentration of 2×10$^{19}$ cm$^{-3}$ or less at 850° C. or more. It was also found that the clathration was reversible and the On$^-$ ion radicals could be released to the atmosphere by increasing or decreasing the temperature. Furthermore, it was demonstrated that by rapidly cooling, the sample from a high temperature of 850° C. or more, C12A17 including On$^-$ ion radicals and OH$^-$ ions at a concentration of 2×10$^{19}$ cm$^{-3}$ or less was obtained.

COMPARATIVE EXAMPLE 1

Mixed powder of CaCO$_3$ and γ-Al$_2$O$_3$ with a molar ratio of 12:7 was subjected to a solid phase reaction at 1300° C. under an atmosphere having a water vapor pressure of 8×10$^{-3}$ atm 10$^{-4}$ MPa, and cooled to room temperature at a rate of 600° C./hr. The resultant powder was isostatic pressed at a pressure of 200 MPa to provide a green compact. The green compact was fired at 1300° C. for 12 to 48 hours under a dry oxygen atmosphere having an oxygen partial pressure of $10^{-1}$ MPa and a water vapor partial pressure of $10^{-5}$ MPa or less. The OH⁻ ion concentration contained in each sample fired for 12, 24 or 48 hours was quantified by infrared absorption spectroscopy.

Figure 9:
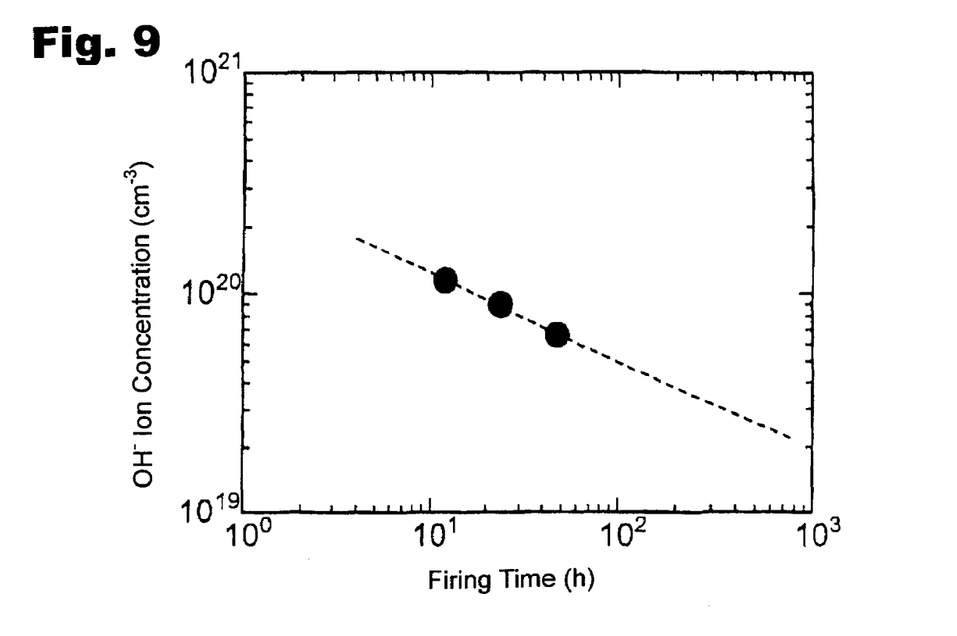
FIG. 9 is a graph showing a change in the concentration of the OH$^-$ ions clathrated in the 12CaO.7Al$_2$O$_3$ compound versus firing time at a temperature of 1300° C.

FIG. 9 shows the firing time dependence of the OH⁻ ion concentration. FIG. 9 reveals that the C12A7 compound synthesized under the atmosphere containing water vapor of at $1 \times 10^{-5}$ MPa or more includes OH⁻ ions at a concentration of $1 \times 10^{20}$ cm⁻³ or more, and that the compound continues to clathrate the OH⁻ ions at a concentration of $1 \times 10^{19}$ cm⁻³ or more when the compound is fired at 1300° C. for 1000 hours under a dry oxygen atmosphere.

In other words, it was found that the compound included the OH⁻ ions at a high concentration of more than $2 \times 10^{19}$ cm⁻³, when the compound was fired at high water vapor pressure, and that, once the OH⁻ ions were clathrated, the concentration of the OH⁻ ions did not decrease in a short time even if the compound was fired under dry oxygen.

INDUSTRIAL APPLICABILITY

The present invention provides a C12A7 compound capable of selectively and reversibly clathrating X⁻ ions, such as active oxygen ion radicals, with improved controllability.

The compound can reversibly clathrate or release On⁻ ion radicals through the elevation or lowering of the temperature thereof in a temperature range of 300 to 850° C. The compound is useful for an oxidation catalyst, an antibacterial agent, an ion conducting material, an electrode for a solid-electrolyte fuel cell, and the like.

The invention claimed is:

1. A $12CaO.7Al_2O_3$ compound clathrating OH⁻ ions at a concentration of $2 \times 10^{19}$ cm⁻³ or less, and On⁻ ion radicals at a high concentration of more than $2 \times 10^{19}$ cm⁻³.

2. A method for preparing the $12CaO.7Al_2O_3$ compound clathrating OH⁻ ions at a concentration of $2 \times 10^{19}$ cm⁻³ or less, and On⁻ ion radicals at a high concentration of more than $2 \times 10^{19}$ cm⁻³, comprising the steps of:

subjecting a mixed material containing calcium (Ca) and aluminum (Al) to a solid phase reaction as a firing temperature not lower than 1200° C. and lower than 1449° C. in a dry oxygen atmosphere having an oxygen partial pressure of $10^{-2}$ MPa or more and a water vapor partial pressure of $10^{-4}$ MPa or less, and slowly cooling the resultant product to a temperature in the range of 300 to 800° C., whereby the compound is provided.

3. A method for preparing the $12CaO.7Al_2O_3$ compound clathrating OH⁻ ions at a concentration of $2 \times 10^{19}$ cm⁻³ or less, and On⁻ ion radicals at a high concentration of more than $2 \times 10^{19}$ cm⁻³, wherein the $12CaO.7Al_2O_3$ compound including minus monovalent ion represented by X⁻ and ion molecules at a concentration of $2 \times 10^{19}$ cm⁻³ or less is kept at a fixed temperature in a temperature range of 300 to 800° C. in a dry oxygen atmosphere having an oxygen partial pressure of $10^{-2}$ MPa or more and a water vapor partial pressure of $10^{-4}$ MPa or less, and is cooled rapidly or slowly to room temperature.

4. A method for reversibly clathrating or releasing On⁻ ion radicals of $12CaO.7Al_2O_3$ compound, comprising:

elevating or lowering temperature of the $12CaO.7Al_2O_3$ compound in a temperature range of 300 to 800° C. in a dry oxygen atmosphere having an oxygen partial pressure of 0.1 atm or more and a water vapor partial pressure of $10^{-3}$ atm or less.

5. A method for preparing the $12CaO.7Al_2O_3$ compound according to claim 2, wherein calcium carbonate, calcium hydroxide, or calcium oxide is used as a raw material for the calcium, and aluminum oxide or aluminum hydroxide is used as a raw material for the aluminum.

* * * * *